US009598290B2

(12) United States Patent
Iaquaniello et al.

(10) Patent No.: US 9,598,290 B2
(45) Date of Patent: Mar. 21, 2017

(54) PROCESS FOR PRODUCING AMMONIA AND UREA

(75) Inventors: Gaetano Iaquaniello, Rome (IT); Barbara Cucchiella, Rome (IT); Elena Antonetti, Rome (IT)

(73) Assignee: STAMICARBON B.V. ACTING UNDER THE NAME OF MT INNOVATION CENTER, Sittard (NL)

( * ) Notice: Subject to any disclaimer, the term of this patent is extended or adjusted under 35 U.S.C. 154(b) by 59 days.

(21) Appl. No.: 14/118,182

(22) PCT Filed: Jun. 25, 2012

(86) PCT No.: PCT/NL2012/050444
§ 371 (c)(1),
(2), (4) Date: Dec. 18, 2013

(87) PCT Pub. No.: WO2012/177137
PCT Pub. Date: Dec. 27, 2012

(65) Prior Publication Data
US 2014/0170052 A1     Jun. 19, 2014

(30) Foreign Application Priority Data

Jun. 23, 2011   (EP) .................................... 11171166

(51) Int. Cl.
C01C 1/04          (2006.01)
C01B 3/02          (2006.01)
(Continued)

(52) U.S. Cl.
CPC ................ *C01C 1/04* (2013.01); *C01B 3/025* (2013.01); *C01B 3/386* (2013.01); *C01B 3/48* (2013.01);
(Continued)

(58) Field of Classification Search
CPC ......... C01C 1/04; C01C 1/0405; C01B 3/025; C01B 3/38; C01B 3/48; C01B 3/36;
(Continued)

(56) References Cited

U.S. PATENT DOCUMENTS 6,448,441 B1    9/2002  Wing-Chiu et al.
7,674,932 B2*   3/2010  Davey ................... C01C 1/0488
                                                  564/63
2004/0028595 A1*  2/2004  Davey ..................... C01B 3/025
                                                  423/361

FOREIGN PATENT DOCUMENTS

DE       102 32 970       2/2003
EP         640559         3/1995
(Continued)

OTHER PUBLICATIONS

International Search Report for PCT/NL2012/050444, mailed Aug. 29, 2012, 2 pages.
(Continued)

*Primary Examiner* — Anthony J Zimmer
(74) *Attorney, Agent, or Firm* — Morrison & Foerster LLP

(57) ABSTRACT

Disclosed is a process for the production of ammonia comprising a step wherein synthesis gas is formed by catalytic partial oxidation. Also disclosed is a process of producing urea, wherein ammonia is formed in a process involving a step of catalytic partial oxidation, and carbon dioxide formed in the same process is reacted with said ammonia so as to form urea.

11 Claims, 2 Drawing Sheets

(51) Int. Cl.
*C01B 3/38* (2006.01)
*C01B 3/48* (2006.01)
*C07C 273/04* (2006.01)

(52) U.S. Cl.
CPC .... *C07C 273/04* (2013.01); *C01B 2203/0261* (2013.01); *C01B 2203/0283* (2013.01); *C01B 2203/0288* (2013.01); *C01B 2203/043* (2013.01); *C01B 2203/047* (2013.01); *C01B 2203/0445* (2013.01); *C01B 2203/0475* (2013.01); *C01B 2203/068* (2013.01); *C01B 2203/127* (2013.01); *C01B 2203/1241* (2013.01); *C01B 2203/148* (2013.01)

(58) Field of Classification Search
CPC ... C01B 3/363; C01B 3/366; C01B 2203/025; C01B 2203/0261; C01B 2203/0283–2203/0294; C01B 2203/042; C01B 2203/043; C01B 2203/0425
See application file for complete search history.

(56) References Cited

FOREIGN PATENT DOCUMENTS

| | | |
|---|---|---|
| EP | 2 186 778 | 5/2010 |
| WO | WO-90/06281 | 6/1990 |
| WO | WO-97/37929 | 10/1997 |
| WO | WO-00/00426 | 1/2000 |
| WO | WO-01/32556 | 5/2001 |
| WO | WO-01/36323 | 5/2001 |
| WO | WO-2007/045457 | 4/2007 |

OTHER PUBLICATIONS

Basini et al., "Catalytic partial oxidation of natural gas at elevated pressure and low residence time," Catalysis Today (2001) 64:9-20.
Basini, "Fuel rich catalytic combustion: Principles and technological developments in short contact time (SCT) catalytic processes," Catalysis Today (2006) 117:384-393.
Chemsystems PERP Program Report Abstract, "Air Separation Technology PERP 08/09S1," Nexant, Inc. (2010) 7 pages.
Hickman and Schmidt, "Production of syngas by direct catalytic oxidation of methane," Science (1993) 259:343-346.
Hickman and Schmidt, "Synthesis Gas Formation by Direct Oxidation of Methane over Pt Monoliths," J Catalysis (1992) 138:267-282.

* cited by examiner

PROCESS FOR PRODUCING AMMONIA AND UREA

CROSS-REFERENCE TO RELATED APPLICATIONS

This application is the national phase of PCT application PCT/NL2012/050444 having an international filing date of 25 Jun. 2012, which claims benefit of European application No. 11171166.9, filed 23 Jun. 2011. The contents of the above patent applications are incorporated by reference herein in their entirety.

FIELD OF THE INVENTION

The invention pertains to a process for the production of ammonia, as well as to a process for producing ammonia and, subsequently, urea.

BACKGROUND OF THE INVENTION

Ammonia is generally produced by reacting hydrogen and nitrogen, according to the following reaction equation:

$$3H_2+N_2 \rightarrow 2NH_3$$

The $H_2$ is generally obtained from synthesis gas (normally known as "syngas"), which in turn is obtained from a hydrocarbon feed material, which is subjected to steam reforming so as to produce a mixture comprising carbon monoxide (CO), hydrogen ($H_2$), and carbon dioxide ($CO_2$), usually followed by a water gas shift reaction wherein carbon monoxide reacts with water so as to form carbon dioxide and hydrogen. After removal of $CO_2$ (or otherwise separating $H_2$ from the gas mixture), the hydrogen is available for reaction with nitrogen ($N_2$). The latter is either present in the original gas mixture (as it is inert with respect to all steps preceding the ammonia synthesis conditions), or added later if obtained from air, in a unit separating nitrogen from oxygen. The hydrogen and nitrogen are subjected to compression and conversion into ammonia in a synthesis reactor.

Ammonia is frequently used as a starting material in the synthesis of urea. Urea ($NH_2CONH_2$) can be produced from ammonia and carbon dioxide at an elevated temperature of, typically, between 150° C. and 250° C. and an elevated pressure of, typically, between 12 and 40 MPa, in the synthesis zone of a urea plant. In this synthesis, two consecutive reaction steps can be considered to take place. In the first step ammonium carbamate is formed, and in the next step, this ammonium carbamate is dehydrated so as to give urea:

$$2NH_3+CO_2 \rightarrow H_2N—CO—ONH_4 \quad (i)$$

$$H_2N—CO—ONH_4 \leftrightarrow H_2N—CO—NH_2+H_2O \quad (ii)$$

A reference process, shown in FIG. 1, for producing ammonia comprises a steam reforming process for producing hydrogen followed by reaction of said hydrogen with nitrogen produced in an air separation unit (ASU). A disadvantage of this process however is that significant energy is used to separate the air into nitrogen and oxygen but no use is made of the oxygen so produced.

Another reference process, such a shown in U.S. Pat. No. 6,448,441, which is incorporated herein by reference, involves the use of two parallel gasifiers, working at different operating conditions, in order to increase the $CO_2$ rate for urea production when a natural gas gasifier is used to produce syngas. By using two gasifiers, it is possible to obtain the correct stoichiometry in the reaction mixture for subsequent production of ammonia. In the process of U.S. Pat. No. 6,448,441, there is a need to produce additional $CO_2$ to obtain the correct stoichiometry for the reaction of ammonia and $CO_2$ to nitrogen. This requires the combustion of additional carbonaceous material, for example natural gas, which consumes more raw materials and energy.

In the production of ammonia, as well as in the production of urea, it is thus desired to be able to present the starting material in the desired stoichiometry, and it is desired to reduce energy and material costs as much as possible.

SUMMARY OF THE INVENTION

In order to better address one or more of the foregoing desires, the invention presents, in one aspect, a process for the production of ammonia, comprising the steps of
(a) providing a hydrocarbon material;
(b) subjecting the hydrocarbon material to catalytic partial oxidation (CPO) so as to produce a synthesis gas comprising carbon monoxide, hydrogen and carbon dioxide;
(c) subjecting the synthesis gas to a water gas shift reaction so as to react carbon monoxide with water under the formation of a gas mixture comprising hydrogen and carbon dioxide.
(d) separating hydrogen from the reaction mixture;
(e) reacting the hydrogen with nitrogen under ammonia-forming conditions so as to produce ammonia, wherein the catalytic partial oxidation is a short contact time catalytic partial oxidation, conducted under a space velocity of 100,000 to 250,000 $hr^{-1}$.

In another aspect, the invention concerns a process for the preparation of urea, comprising a process for the preparation of ammonia as defined above, removing $CO_2$ from the reaction mixture, and reacting the ammonia with the removed $CO_2$, under urea-forming conditions.

DETAILED DESCRIPTION OF THE INVENTION

Figure 1:
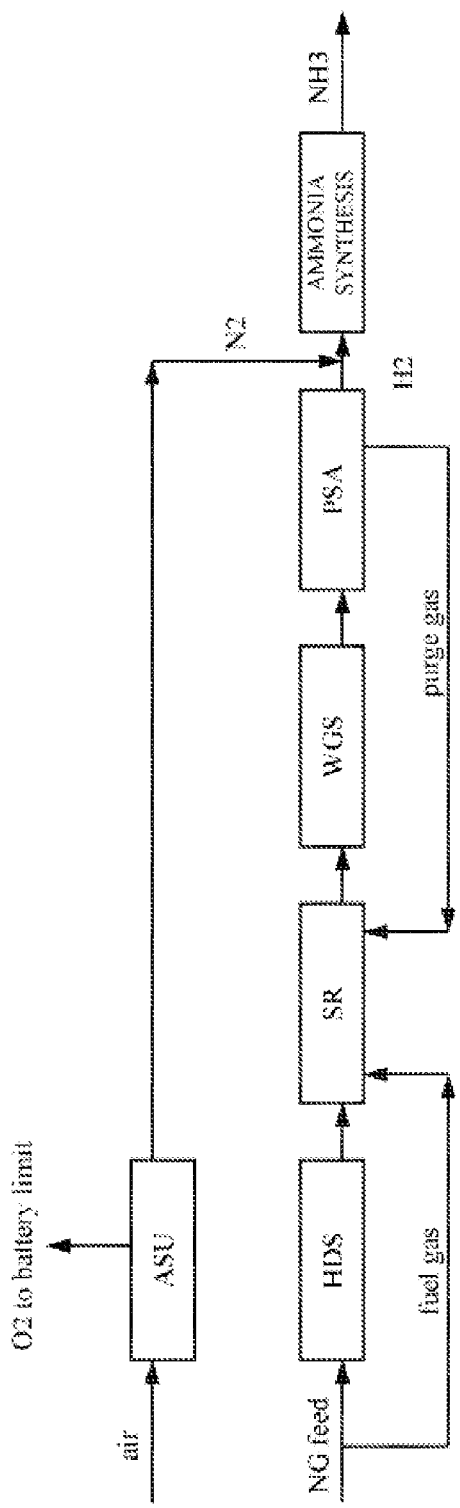
FIG. 1 is a schematic representation of an embodiment known to the art

In a broad sense, the invention is based on the judicious insight that the use of catalytic partial oxidation in the formation of synthesis gas, rather than steam reforming, is able to bring about unexpected advantages in both the production of ammonia and the production of urea.

The CPO reaction is known to the skilled person. It will generally be carried out in a catalytic partial oxidation reactor, comprising a suitable catalyst bed that serves to catalyze the partial oxidation of hydrocarbon into CO and $H_2$. It will be understood that some complete oxidation product (viz. $CO_2$) may also be formed.

The term CPO (also often referred to as SCT-CPO) is known to the skilled person. SCT-CPO refers to Short Contact Time Catalytic Partial Oxidation. The CPO reaction takes place in a reactor under the influence of a catalyst at residence times between $10^{-2}$ to $10^{-4}$ and with typical catalyst surface contact times around $10^{-6}$ $s^{-1}$. These contact time correspond to typical space velocities of 100,000 to 250,000 $hr^{-1}$ preferably 100,000 to 200,000 $hr^{-1}$. Catalysts employed for SCT-CPO comprise Ni, Pd, Pt, Rh, or Ru. The reaction takes place at catalyst surface temperatures above 950° C., preferably above 1000° C. By employing said short contact times and high catalyst surface temperatures the formation of CO his highly favoured and the formation of carbon or $CO_2$ is suppressed. This leads to a highly favourable synthesis gas composition. A reference to CPO is (a) L. Basini, Catalysis Today 117 (2006) 384-393. Other references include (b) L. Basini, K. Aasberg-Petersen, A. Guarinoni, M. Oestberg, Catalysis Today (2001) 64, 9-20 "Catalytic Partial Oxidation of Natural Gas at Elevated Pressure and Low Residence Time"; (c) H. Hickman, L. D. Schmidt, J. Catal. 138 (1992) 267; (d) D. Hichman, L. D. Schmidt Science, 259 (1993) 343; (e) L. Basini, G. Donati WO 97/37929; (f) Sanfilippo, Domenico; Basini, Luca; Marchionna, Mario; EP-640559; (g) D. Schaddenhorst, R. J. Schoonebeek; WO 00/00426; (h) K. L. Hohn, L. D. Schmidt, S. Reyes, J. S. Freeley, WO 01/32556; (i) A. M. Gaffney, R. Songer, R. Ostwald, D. Corbin, WO 01/36323.

The production of ammonia requires the availability of nitrogen ($N_2$) as a reactant. Nitrogen is obtained from air, and in regular processes this results in oxygen ($O_2$) being lost. In the present invention, it is judiciously foreseen that oxygen yielded by providing nitrogen as a reactant, is used as the source of oxidation oxygen in the catalytic partial oxidation step. Thus, the combination, according to the invention, of a catalytic partial oxidation step and the synthesis of ammonia, presents a highly economical advancement. This presents in fact a synergy, in the sense that the oxygen required for catalytic partial oxidation is available by virtue of the production of ammonia and, put otherwise, oxygen normally lost can now be used.

In steam reforming, which is endothermic, usually a fuel is combusted in order to provide the energy input required for the reaction. The $CO_2$ that results from the fuel combustion, in steam reforming will be lost, as it is not available for any use, and thus needs to be vented into the atmosphere. Or, a major investment would have to be made in order to add a separate $CO_2$ recovery unit. Whilst dispensing with the need for such a fuel is an advantage per se of conducting catalytic partial oxidation instead, it brings about an additional effect that can be put to use in accordance with the present invention. The production of urea requires the availability of carbon dioxide ($CO_2$) as a reactant. Any $CO_2$ formed in the catalytic partial oxidation, and particularly from the subsequent step of a water gas shift reaction, is present in the stream of gases that is part of a production process, and is therewith directly available as a reactant for the production of urea.

The process of the invention, whether for producing ammonia or for producing urea, starts with the catalytic partial oxidation of a hydrocarbon material. The hydrocarbon material can be a single hydrocarbon, a mixture of hydrocarbons, or any other composition comprising at least one hydrocarbon. Preferred sources are natural gas ($CH_4$), liquid hydrocarbons (such as naphta), gasification of coal, biomass, and waste-to-energy gasification facilities. As conventional, in the event that natural gas is employed, this will generally be desulphurized before being subjected to the process of the invention.

The hydrocarbon material can be in a gaseous (e.g. methane or natural gas) and/or in a liquid state and also from biomass. The hydrocarbon material may be suitable for direct feed to the CPO or can be pre-treated for removal of any impurities, such as sulphur compounds, that might be present.

Preferably, the hydrocarbon material is selected from the group consisting of natural gas, Liquefied Petroleum Gas (LPG), refinery gas, naphtha, and mixtures thereof.

CPO reactors are known to the skilled person. A CPO reactor generally comprises a reaction zone, made up of a vertical cylindrically shaped steel pressure vessel lined with a refractory material. A CPO reactor typically is distinguished from an autothermal reformer reactors, as the latter comprises a burner, which a CPO generally does not.

A mixer, such as shown in WO2007045457 may be used to introduce feed streams into the reactor.

The CPO process results in synthesis gas, or syngas, comprising CO, $CO_2$ and $H_2$. With reference to methane as an exemplary hydrocarbon feed material, the reaction equation for the CPO process is:

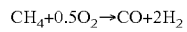

$$CH_4 + 0.5O_2 \rightarrow CO + 2H_2$$

The CPO reaction is known to the skilled person. It will generally be carried out in a catalytic partial oxidation reactor, comprising a suitable catalyst bed that serves to catalyze the partial oxidation of hydrocarbon into CO and $H_2$. It will be understood that some complete oxidation product (viz. $CO_2$) may also be formed.

The term CPO (also often referred to as SCT-CPO) is known to the skilled person. SCT-CPO refers to Short Contact Time Catalytic Partial Oxidation. The CPO reaction takes place in a reactor under the influence of a catalyst at residence times between $10^{-2}$ to $10^{-4}$ and with typical catalyst surface contact times around $10^{-6}$ $s^{-1}$. These contact time correspond to typical space velocities of 100,000 to 250,000 $hr^{-1}$ preferably 100,000 to 200,000 $hr^{-1}$. Catalysts employed for SCT-CPO comprise Ni, Pd, Pt, Rh, or Ru. The reaction takes place at catalyst surface temperatures above 950° C., preferably above 1000° C. By employing said short contact times and high catalyst surface temperatures the formation of CO his highly favoured and the formation of carbon or $CO_2$ is suppressed. This leads to a highly favourable synthesis gas composition. A reference to CPO is (a) L. Basini, Catalysis Today 117 (2006) 384-393. Other references include (b) L. Basini, K. Aasberg-Petersen, A. Guarinoni, M. Oestberg, Catalysis Today (2001) 64, 9-20 "Catalytic Partial Oxidation of Natural Gas at Elevated Pressure and Low Residence Time"; (c) H. Hickman, L. D. Schmidt, J. Catal. 138 (1992) 267; (d) D. Hichman, L. D. Schmidt Science, 259 (1993) 343; (e) L. Basini, G. Donati WO 97/37929; (f) Sanfilippo, Domenico; Basini, Luca; Marchionna, Mario; EP-640559; (g) D. Schaddenhorst, R. J. Schoonebeek; WO 00/00426; (h) K. L. Hohn, L. D. Schmidt, S. Reyes, J. S. Freeley, WO 01/32556; (i) A. M. Gaffney, R. Songer, R. Ostwald, D. Corbin, WO 01/36323.

It will be understood, that in a CPO process, oxygen is to be provided in order to effect the oxidation. Whilst the oxygen can be in the form of air, a drawback thereof is that this means that a relatively large amount of nitrogen, which is inert until the ammonia-forming reaction, will have to be carried through the process. This requires a much larger equipment than would be strictly necessary for the reactions to be conducted, which is economically undesirable, and is associated with other drawbacks such as a need for building a facility occupying an unduly large ground surface area In this respect it is preferred that the catalytic partial oxidation is conducted under the influence of an oxygen-containing gas-stream comprising at least 40% oxygen, preferably at least 60% oxygen. More preferably, the oxygen-containing gas-stream is oxygen having a purity of from 90%-100%.

A further advantage of using catalytic partial oxidation, is that a synthesis gas can be produced having the proper $H_2/CO_2$ ratio to maximize the yield of ammonia and urea in relation to the feed composition. By properly setting the steam to carbon (S/C) and oxygen to carbon ($O_2$/C) ratio and preheating temperatures of the streams to the CPO reactor, also in presence of a natural gas feed, the amount of $CO_2$ produced in the synthesis gas is sufficiently high to use all of the produced $NH_3$, without any external support or excess of $NH_3$. The skilled person is aware, without undue experimentation, how to calculate the proper amounts of reactants needed in the synthesis gas, and how to set the catalytic partial oxidation process so as to achieve this.

The CPO reactor preferably is operated with a steam to carbon ratio (S/C) in the range of 0.3-1.0, more preferably in the range of 0.4 to 0.6. The oxygen to carbon ratio (O/C) preferably is in the range of 0.3-1.0, more preferably in the range of 0.5-0.7.

In a further preferred embodiment, the raw gas obtained from the catalytic partial oxidation has a temperature between about 900° C. and 1200° C., preferably between 950-1050° C., better around 1000° C.

For the purpose of producing hydrogen, the mixture is subjected to a water gas shift reaction. To this end, the mixture is routed to a water gas shift reactor (WGSR), wherein the gas mixture comprising carbon monoxide and steam is converted to hydrogen and carbon dioxide. The synthesis gas is generally cooled down, either in a process gas boiler or in a direct quencher, before entering the WGS reactor, producing a shifted synthesis gas stream. In the above example, starting from $CH_4$, this subsequent step of converting CO into $CO_2$ by means of a water gas shift reactor is represented by the following reaction equation:

$$CO + 2H_2 + H_2O \rightarrow CO_2 + 3H_2$$

The WGS reaction is typically carried out using either a single stage or multi stage to attain the desired degree and rate of conversion. In a multi stage process, the high temperature stage (HTS) operates at 300-450° C. and typically in the presence of an iron-based catalyst such as Fe/Cr. In the HTS the largest amount of CO is converted, usually more than 90% such as between 96 and 98%. The following stage can be a high, medium or low temperature stage (HTS, MTS or LTS); using MTS or LTS the operating temperature is about 180-280° C. and typically a copper/zinc catalyst supported on alumina (Cu/Zn/Al) catalyst is used. In these latter stages the residual CO concentration in the outlet stream is typically as low as 0.1-0.3%.

The gas stream resulting from the WGSR contains mainly hydrogen and carbon dioxide. Optionally, hydrogen is separated from this stream by pressure swing absorption (PSA) to yield a pure hydrogen stream and a purge gas stream (which typically comprises $H_2$, $CH_4$, CO, and $CO_2$). The purge gas from PSA is recycled to the CPO reactor in order to have a 100% conversion of the feed.

In a first aspect, the process of the invention is used for the production of ammonia. This requires providing hydrogen as a reactant, in accordance with the aforementioned step (d), viz. separating hydrogen from the reaction mixture. Preferably, the separation of hydrogen from the reaction mixture resulting from the water gas shift reaction by removing $CO_2$ from the gas mixture comprising hydrogen and carbon dioxide, so as to obtain a gas mixture enriched in $H_2$. The latter is reacted with $N_2$ so as to form ammonia. This reaction is well-known, and the skilled person is familiar with production methods and plants to carry this out.

In the process of the invention it is preferred that the oxygen used in the catalytic partial oxidation and the nitrogen used in the ammonia-forming reaction are obtained from an air separation unit.

In connection herewith, in one separate aspect, the invention pertains to a process for the production of ammonia, comprising the steps of (a) providing a hydrocarbon material;

(b) subjecting the hydrocarbon material to catalytic partial oxidation (CPO) so as to produce a synthesis gas comprising carbon monoxide, hydrogen and carbon dioxide;

(c) subjecting the synthesis gas to a water gas shift reaction so as to react carbon monoxide with water under the formation of a gas mixture comprising hydrogen and carbon dioxide.

(d) separating hydrogen from the reaction mixture;

(e) reacting the hydrogen with nitrogen under ammonia-forming conditions so as to produce ammonia, wherein the oxygen used in the catalytic partial oxidation and the nitrogen used in the ammonia-forming reaction are obtained from an air separation unit. Preferably, herein $H_2$ is purified using a Pressure Swing Absorber after $CO_2$ removal, to yield a pure hydrogen stream and a purge gas stream and, more preferably, the purge gas from PSA is recycled to the CPO reactor.

It will be understood that in the foregoing separate aspect of the invention, the catalytic partial oxidation should preferably be understood as it is understood in the art, viz. as being of the above-explained short contact time (SCT) type.

This brings about the advantage that no nitrogen needs to be carried through in the process, and the components of the air separated both are used to the maximum extent possible, rather than venting oxygen (in the case of using nitrogen in the ammonia-forming reaction) or burdening the process with a large amount of inert nitrogen (in the case of using air in the catalytic partial oxidation).

In an air separation unit, nitrogen and oxygen are produced generally according to the following equation:

$$1.88N_2 + 0.5O_2(air) \rightarrow 1.88N_2 + 0.5O_2$$

Air separation units (commonly known as ASUs) are known to the skilled person. Air separation units employing cryogenic, adsorption air separation, vacuum swing adsorption or membrane air separation may be used. In a preferred embodiment a cryogenic air separation process is used as it can yield highly pure nitrogen and oxygen. In the process large volumes of air from the atmosphere are compressed, cooled and liquefied. After compression impurities are removed and the nitrogen and oxygen are separated by distillation. A comprehensive overview may be found in the Nexant PERP 08/09S1 (February 2010) report. It will be understood that the oxygen and the nitrogen can also be produced in different air separation units. Preferably, the nitrogen and the oxygen used in the process come from the same air separation unit.

In a second aspect, the process of the invention is used for the production of urea. The ammonia is then reacted with the removed $CO_2$ under urea-forming conditions. This reaction too is well-known, and production methods and plants are available to the skilled person.

Urea ($NH_2CONH_2$) can be produced from ammonia and carbon dioxide at an elevated temperature (typically, between 150° C. and 250° C.) and elevated pressure (typically between 12 and 40 MPa) in the synthesis zone of a urea plant. In this synthesis, two consecutive reaction steps can be considered to take place. In the first step ammonium carbamate is formed, and in the next step, this ammonium carbamate is dehydrated so as to give urea, The first step (i) is exothermic, and the second step can be represented as an endothermic equilibrium reaction (ii):

$$2NH_3 + CO_2 \rightarrow H_2N\text{---}CO\text{---}ONH_4 \qquad (i)$$

$$H_2N\text{---}CO\text{---}ONH_4 \leftrightarrow H_2N\text{---}CO\text{---}NH_2 + H_2O \qquad (ii)$$

In a typical urea production plant, the foregoing reactions are conducted in a urea synthesis section so as to result in an aqueous solution comprising urea. In one or more subsequent concentration sections, this solution is concentrated to eventually yield urea in a form of a melt rather than a solution. This melt is further subjected to one or more finishing steps, such as prilling, granulation, pelletizing or compacting.

By the judicious involvement of catalytic partial oxidation prior to a water gas shift reaction, and particularly in conjunction with the use of an air separation unit, the invention provides a very economical way of using the components of the gas mixture obtained, in producing the important bulk chemical compound, urea. The excess of nitrogen from the air separation unit may be used within the production facilities or sold to other users.

The present invention will further be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a" or "an", "the", this includes a plural of that noun unless something else is specifically stated. Unless otherwise indicated percentages are volume percent and ratios (for example Steam/Carbon or Oxygen/Carbon) are on a vol %/vol % basis.

DETAILED DESCRIPTION OF THE DRAWINGS

In FIG. 1 a typical representation is given of an embodiment known in the art.

A feed gas stream enters a desulphurisation unit. The resulting stream is mixed with steam and fed to the steam reforming reactor (SR).

The syngas at the outlet of SR is cooled down and then introduced into a water gas shift section.

The resulting shifted gas is cooled down and purified into a Pressure Swing Absorption (PSA) unit producing an ultra pure hydrogen stream and a purge gas which is burnt in the SR furnace.

Pure hydrogen is mixed with a nitrogen stream in a ratio of about 3:1 before being compressed and introduced into the ammonia synthesis reactor. Nitrogen is obtained from the Air Separation Unit (ASU) where also an oxygen stream is produced.

Figure 2:
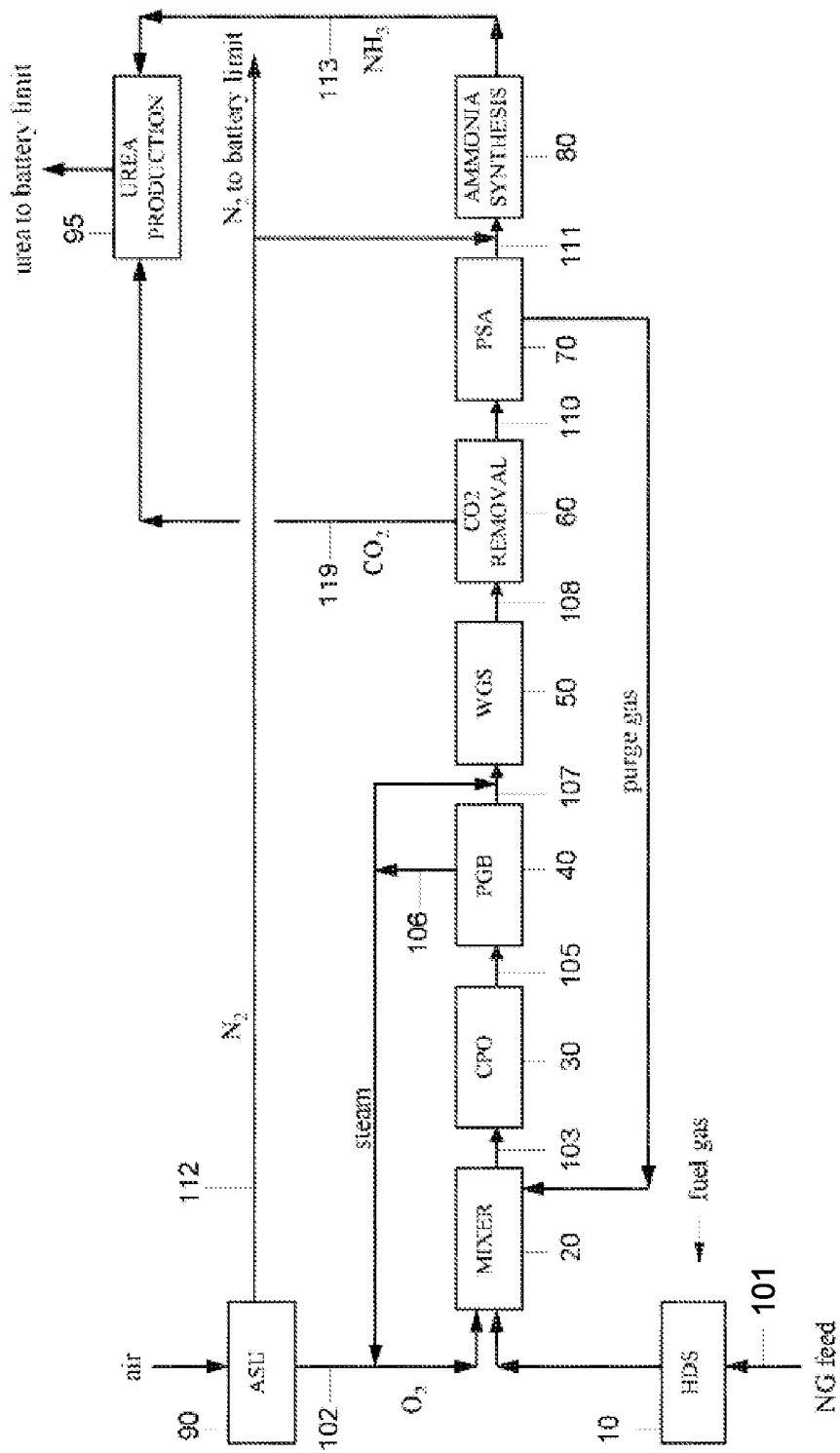
FIG. 2 is a schematic representation of an embodiment of the present invention

In FIG. 2, one embodiment of the present invention is presented. A feed gas stream 101 enters a desulphurisation unit 10 after mixing with stream 103, the purge gas from PSA. It is remarked that stream 103 is not correctly as shown in the figure, and should flow to upstream of unit 10 where it is mixed with stream 101. The resulting stream is mixed in a proper device, 20, with another stream containing oxygen and steam (resulting from mixing stream 102 and steam) before being fed to the CPO reactor as feed stream to unit 30. In one embodiment of the present invention, a pre-reformer (not shown) is upstream of CPO reactor 30.

The CPO reactor 30 may be a steel vessel internally lined for converting hydrocarbons, such as natural gas, LPG, refinery gas, naphta and even heavier feed. The CPO reactor preferably operates with a steam to carbon ratio (S/C) in the range of 0.3-1.0, preferably in the range of 0.4 to 0.6. The oxygen to carbon ratio ($O_2/C$) preferably is in the range of 0.4-1.0, more preferably in the range of 0.5-0.7.

The syngas at the outlet of the CPO reactor preferably is in the temperature range of 800° C.-1200° C., more preferably between 900° C. and 1050° C. The syngas stream 105 is cooled by indirect heat exchange raising steam 106 in a process gas boiler 40 (in an alternative embodiment it may be cooled by a direct water quenching). The quenched syngas 107 is then introduced into a CO shift reactor 50. The shift reactor 50 may be in one stage or two stages with an intercooler (in a alternative embodiment it may be an isothermal shift convertor). Shift reactor 50 typically uses, e.g., an iron based catalyst and/or a copper based catalyst.

The resulting shifted gas 108 is cooled down and introduced into a $CO_2$ removal unit 60 where all of the $CO_2$ goes into a stream 109. The $CO_2$ removal unit 60 may be a solvent wash system, such as amine, selexol or other know solvents, or by other means known to the skilled person. The amount of $CO_2$ may be varied but for a ammonia/urea production plant, it will be as high as possible.

The raw hydrogen gas is then purified in a pressure Swing Absorption (PSA) unit 70 producing an ultra pure hydrogen stream 111 and a purge gas 103 which after compression is recycled to the CPO reactor 30, A complete recycle of the purge gas will yield almost 100% conversion of the carbon fraction of the feed to $CO_2$ and 100% of $H_2$ recovery and use.

The present invention enables recovering almost 100% of the total carbon dioxide generation from high pressure syngas as opposed to the 50-60% of a more conventional steam reforming (SR) technology. The carbon dioxide recovery from high pressure syngas stream is much easier, without major severe corrosion issues and it is much less expensive. Utility and energy requirements are significantly lower compared to flue gas $CO_2$ recovery systems.

Pure hydrogen 111 is mixed with a nitrogen stream in a ratio of about 3:1 before being compressed and introduced into the ammonia synthesis reactor. Nitrogen is obtained from the Air Separtion Unit (ASU) 90 where also the oxygen stream 102 is produced. In another embodiment streams 112 and 102 are produced in different ASUs. As embodied herein, any process for ammonia synthesis may be used. The most common industrial process for ammonia synthesis involving forming a mixture of gaseous nitrogen and hydrogen in a 1 to 3 ratio, plus minor components as $CH_4$ and $CO_2$.

The present invention allows to feed to the synthesis reactor pure components and minimizing any purge. This results in improved energy efficiency of the overall manufacturing process. The mixture compressed at higher pressure, e.g. in the range of 80-200 barg, reacts in accordance with the following reaction:

$$3H_2 + N_2 \rightarrow 2NH_3$$

The produced ammonia is then combined with the $CO_2$ removed from the syngas and sent to a urea production unit, 95. As embodied herein, any process for urea synthesis may be used. In a common urea synthesis process, the ammonia and $CO_2$ are fed into the synthesis section to form ammonia carbamate in accordance with the exotermic reaction:

$$2NH_3 + CO_2 = NH_2COONH_4$$

A fraction of ammonium carbamate then dehydrates to form urea and water in accordance with the endothermic reversible reaction:

$$NH_2COONH_4 = (NH_2)2CO + H_2O$$

The invention claimed is:

1. A process for the production of urea, comprising the steps of
   (a) providing a hydrocarbon material;
   (b) subjecting the hydrocarbon material to catalytic partial oxidation (CPO) by reaction with an oxygen-containing gas stream in a CPO reactor so as to produce a synthesis gas comprising carbon monoxide, hydrogen and carbon dioxide;
   wherein said catalytic partial oxidation is a short contact time catalytic partial oxidation, conducted under a space velocity of 100,000 to 250,000 hr$^{-1}$;
   (c) subjecting the synthesis gas to a water gas shift reaction so as to react carbon monoxide with water to form a gas mixture comprising hydrogen and carbon dioxide;
   (d) recovering $CO_2$ from the gas mixture of (c), so as to obtain said recovered $CO_2$ and a gas mixture enriched in hydrogen;
   (e) purifying hydrogen from said gas mixture enriched in hydrogen using a pressure swing absorber, to yield a pure hydrogen stream and a purge gas stream; and
   (f) reacting the hydrogen of (e) with nitrogen under ammonia-forming conditions so as to produce ammonia; and
   (g) combining the ammonia produced in (f) with the recovered $CO_2$ from (d) to produce urea; and
   wherein air supplied to a single air separation unit provides the oxygen-containing gas stream used in the catalytic partial oxidation and the nitrogen used in the ammonia-forming reaction; and
   wherein the entire purge gas stream is recycled to the CPO reactor.

2. A process according to claim 1, wherein the space velocity is 100,000 to 200,000 hr$^{-1}$.

3. A process according to claim 1, wherein the oxygen-containing gas stream in (b) comprises at least 40% v/v oxygen.

4. A process according to claim 1, wherein the oxygen-containing gas stream in (b) comprises at least 90%-100% v/v oxygen.

5. A process according to claim 1 comprising further purifying hydrogen by methanation of CO and $CO_2$.

6. A process according to claim 1, wherein the hydrocarbon material is selected from the group consisting of natural gas, Liquefied Petroleum Gas (LPG), refinery gas, naphtha, and mixtures thereof.

7. A process according to claim 1, wherein the oxygen to carbon ratio in the catalytic partial oxidation is between 0.3 and 0.7.

8. A process according to claim 1, wherein the synthesis gas obtained from the catalytic partial oxidation has a temperature between about 900° C. and 1200° C.

9. The process of claim 3 wherein the oxygen-containing gas stream comprises at least 60% v/v oxygen.

10. The process of claim 1, wherein the steam-to-carbon (S/C), oxygen-to-carbon ($O_2$/C) ratio and preheating temperatures of the streams to the CPO reactor are adjusted so that the amount of $CO_2$ produced in the synthesis gas is sufficiently high to use all of the ammonia produced in (f) without any additional ammonia or excess ammonia to produce urea in step (g).

11. The process of claim 10, wherein the S/C is 0.4-0.6, the $O_2$/C is 0.5-0.7.

* * * * *